US00PP32720P2

(12) United States Plant Patent
Bonany et al.

(10) Patent No.: US PP32,720 P2
(45) Date of Patent: Jan. 5, 2021

(54) APPLE TREE NAMED 'HOT84A1'

(50) Latin Name: *Malus domestica*
Varietal Denomination: HOT84A1

(71) Applicants: The New Zealand Institute for Plant and Food Research Limited, Auckland (NZ); Institut De Recerca I Tecnologia Agroalimentaries (IRTA), Barcelona (ES); FruitFutur A.I.E., Lleida (ES)

(72) Inventors: Joan Bonany, Lleida (ES); Richard Volz, Havelock North (NZ)

(73) Assignees: The New Zealand Institute for Plant and Food Research Limited, Auckland (NZ); Institut De Recerca I Tecnologia Agroalimentaries (IRTA), Barcelona (ES); FruitFutur A.I.E., Lieida (ES)

( * ) Notice: Subject to any disclaimer, the term of this patent is extended or adjusted under 35 U.S.C. 154(b) by 0 days.

(21) Appl. No.: 16/873,543

(22) Filed: Apr. 30, 2020

(51) Int. Cl.
*A01H 6/74* (2018.01)
*A01H 5/00* (2018.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Leydig, Voit & Mayer, Ltd.

(57) ABSTRACT

A new and distinct apple variety of *Malus domestica* named 'HOT84A1' and characterized by its attractive appearance, its dark red color, and is notable for its long storage life. The variety results from crossing the apple varieties 'Scired' (not patented) and 'Scilate' (U.S. Plant Pat. No. 20,477) in Havelock North, New Zealand.

2 Drawing Sheets

Genus and species plant named: *Malus domestica.*
Variety denomination: 'HOT84A1'.

BACKGROUND OF THE INVENTION

The new plant variety described herein resulted from a selection from a population of seedlings derived from the controlled crossing of the apple varieties 'Scired' (not patented) (seed parent) and 'Scilate' (U.S. Plant Pat. No. 20,477) (pollen parent). The planned cross was made in 2002 on trees located in Havelock North, Hawke's Bay, New Zealand and the seed transported and sown in plots in Gimenells near Lleida, Catalonia, Spain. 'HOT84A1' was selected in 2007 as a single plant from among a population of seedlings and was selected for its attractive appearance, good flavor, texture and storage. It was asexually propagated first in Lleida, Spain by budding onto M9 rootstock. The variety has since been observed over three asexually propagated generations and found to remain true to type.

SUMMARY OF THE INVENTION

'HOT84A1' is characterized by its attractive fruit with good texture and flavor, harvesting in early October in Spain. Under growing conditions in Spain 'HOT84A1' is distinguished from other apple varieties due to the following unique characteristics: Compared to 'Fuji', 'HOT84A1' has an earlier harvest season by approximately 2 weeks, and a significantly higher proportion of the skin surface is covered by over color, 70-90%, compared to 'Fuji', 40-50%.

Under the growing conditions in Spain the new variety was able to be distinguished from its parents 'Scired' and 'Scilate', by the following characteristics:

'Scilate': The time of eating maturity is later than 'HOT84A1'.

'Scired': 'HOT84A1' fruit is larger than 'Scired' apples. In addition 'HOT84A1' has a fruit skin overcolor pattern of a solid flush with weakly defined stripes; compared to 'Scired' which has a solid flush overcolor pattern.

Asexual reproduction of this new variety by budding and grafting shows that the aforementioned characteristics are true to form and are established and transmitted through succeeding propagation. This is true of buds grafted onto M9 rootstocks.

BRIEF DESCRIPTION OF PHOTOGRAPHS

The accompanying photographs show typical specimens of the tree, foliage and fruit of the new variety as depicted in colors as nearly true as is reasonably possible to make the same in a color illustration of this character.

DETAILED DESCRIPTION

Figure 1:
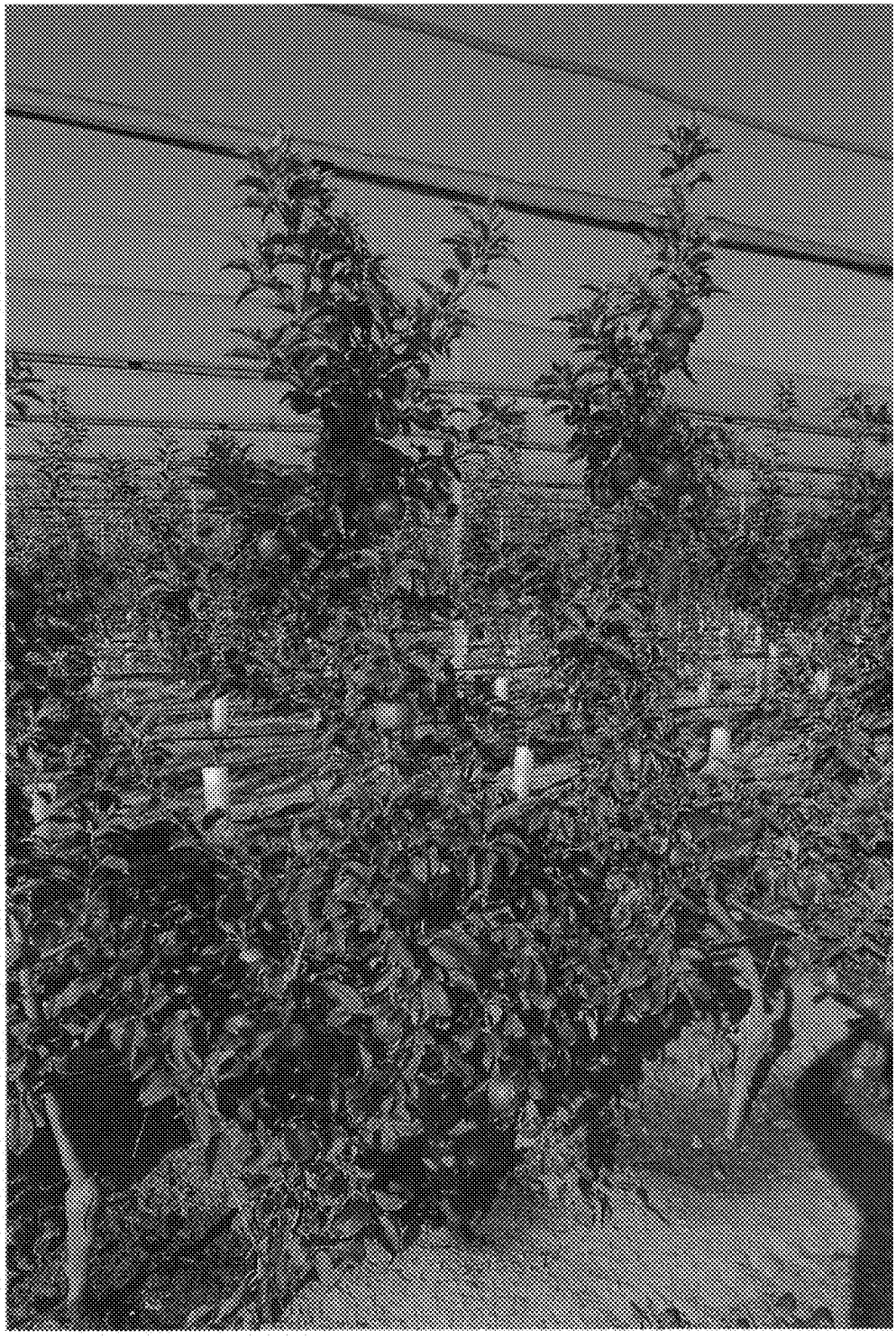
FIG. 1 shows a 3 year old tree of 'HOT84A1' scion on M9 rootstock in the field.
Figure 2:
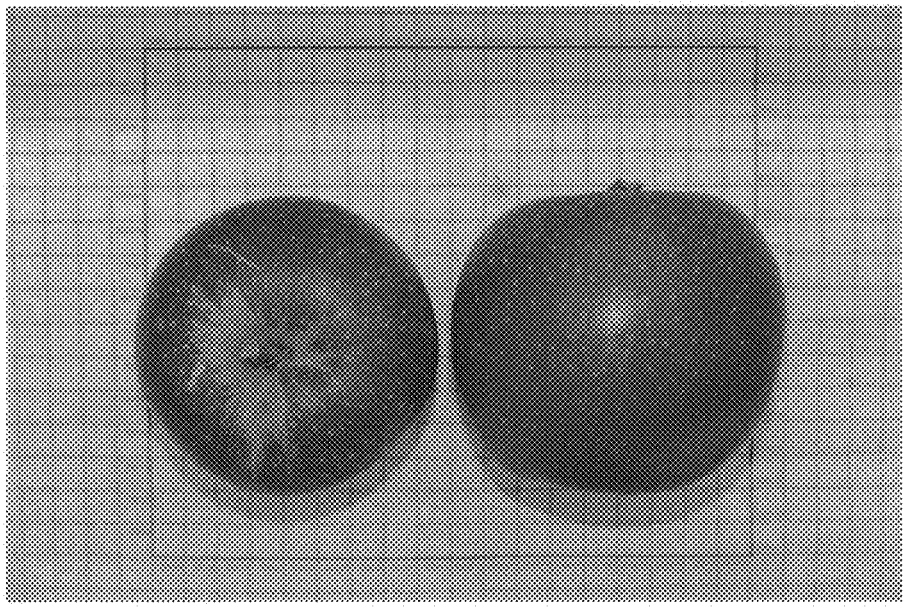
FIG. 2 shows whole 'HOT84A1' fruit.
Figure 3:
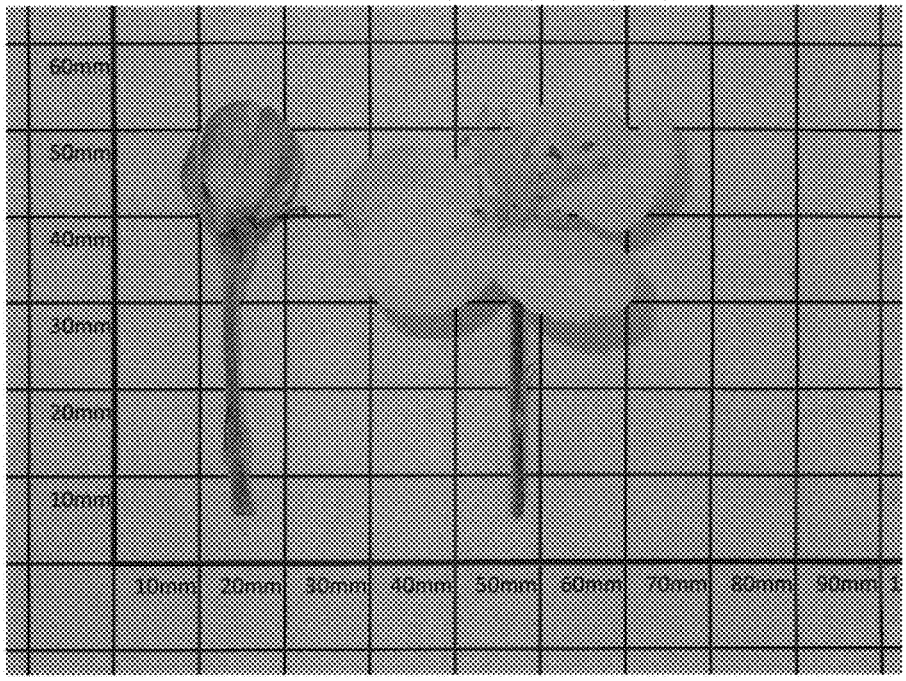
FIG. 3 shows 'HOT84A1' flower

The following is a description of the new variety with color terminology in accordance with The Royal Horticultural Society Color Charts (R.H.S.C.C.) fifth edition.

The specimens described were grown at Lleida, Catalonia, Spain. The observations were made over several seasons from 2014-2018 season on 5-9 year old trees.

Tree: Ramified growth habit, approximately 2.7 m tall and 1.4 m wide; spreading habit; bearing on spurs and long shoots; medium vigor on M9 rootstock, managed under standard orchard practice.

Trunk: Measurements were taken 20 cm from the graft union. Trunk circumference approximately 19.5 cm; color near dark grey 197C; bark texture both smooth and rough texture.

One year old shoot: Approximately 24 cm long, medium thickness with straight growth; color on the sunny side near dark brown 166A; average internode length 3.2 cm; number of lenticels were sparse, round in shape and near grey brown 199D and approximately 0.95 mm in diameter Leaves: Average length 8.5 cm; average width 5 cm at the widest point; upper side of the blade near dark brown green N137D; underside near brown green 138B with medium pubescence; basal shape cordate; apex shape right angled; margin of the leaves serrate; the attitude in relation to the shoot upwards. Vegetative bud burst early March.

Petiole: Average length 32.6 mm; average width 2.2 mm.

Stipule: Average length 6.7 mm; average width 1.1 mm; shape small and elongated; color near brown green 137C on the upper side; under side color of the stipules near brown green 138B.

Flowers: Color at balloon stage near dark pink, near 63A; diameter of the open flower approximately 17.9 mm; petals were not touching, and there were five flowers per cluster; time of beginning of flowering early April, followed by full bloom on the approximately 8th April.

Petals: Five petals per flower with a circular shape; average length 18.7 mm; average width 16.4 mm; with a rounded base; lower surface coloration near white NN155B with near purple veins 71C.

Stamen: Average of 20 per flower. Filaments near white 155C and average length 11.4 mm. Anthers average length of 2.8 mm; average width 1.7 mm; color near light yellow 11B. Pollen color near yellow 3A. Anther position above stigma.

Carpel: Average length 12.1 mm; exterior color near light green 149C.

Pedicel: Average length 26.5 mm; average diameter 1.4 mm; color near green 144A.

Sepals: Five sepals per flower; overall shape of an acute and curved triangle; smooth margin; average length 7.1 mm; average width 4.7 mm; color near green 144A.

Fruit size: Large to very large; average width 75 mm; average height 87.5 mm; average weight 298 g.

Shape: Oblong; position of maximum diameter middle; crowning at calyx end absent to weak. Eye basin average depth 18.4 mm; average width 36.9 mm.

Skin: Medium hard texture; ribbing absent or weak; bloom of skin absent or weak; greasiness of skin absent or weak; background color near yellow 8B; number of lenticels many; size of lenticels large.

Over color: Approximately 70% of skin surface; near dark purple red 46A; pattern of overcolor solid flush with weakly defined stripes; width of stripes medium; large amount of russet around stalk cavity; amount of russet on cheeks medium; area of russet around eye basin medium;

Stalk: Average length 21.9 mm; average width 3 mm; curvature absent or very weak. Average depth of stalk cavity 17.7 mm; average width 35.1 mm.

Flesh: Firm, average fruit firmness 8.8 kgf; very juicy; near light yellow 5D.

Flavor: Sweet wine; aroma sweet apple; soluble solids 17%.

Seeds: Five locules; medium seed size; average length 7.8 mm; average width 5 mm; color near dark brown 177A.

Harvest: Late September-early October.

Use: Dessert. Adapted to hot climate growing conditions. Less sensitive to sunburn and cracking than 'Fuji'.

Keeping quality: Excellent, up to 8 months at 0.5° C.+1 week shelf life.

The invention claimed is:

1. A new and distinct apple tree substantially as illustrated and described herein.

* * * * *